US006884599B2

(12) United States Patent
Pace

(10) Patent No.: US 6,884,599 B2
(45) Date of Patent: Apr. 26, 2005

(54) KIT FOR THE DETERMINATION OF L-CARNITINE IN BIOLOGICAL FLUIDS AND TISSUES

(75) Inventor: Silvia Pace, Pomezia (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 0 days.

(21) Appl. No.: 10/240,711

(22) PCT Filed: Mar. 30, 2001

(86) PCT No.: PCT/IT01/00166
§ 371 (c)(1),
(2), (4) Date: Oct. 4, 2002

(87) PCT Pub. No.: WO01/79532
PCT Pub. Date: Oct. 25, 2001

(65) Prior Publication Data
US 2003/0129682 A1 Jul. 10, 2003

(30) Foreign Application Priority Data
Apr. 13, 2000 (IT) ................ RM 2000A000195

(51) Int. Cl.[7] ................ C12Q 1/48; C12N 9/15; G01N 33/53
(52) U.S. Cl. ................ 435/15; 435/193; 435/975; 436/815
(58) Field of Search ................ 435/15, 975, 193; 436/815; 424/94.5

(56) References Cited

U.S. PATENT DOCUMENTS 5,316,917 A    5/1994   Roe ................ 435/15
6,027,690 A    2/2000   Bair ................ 422/61

OTHER PUBLICATIONS

Sigma Catalog, 1998, p. 1874.*
Wieland et al. "Free and esterified carnitines: Colorimetric method" Meth. Enz. anal. (1985) 8:481–8.*
Webster's II New Riverside Dictionary 1994 Houghton–Mifflin: Boston, p. 667.*
Indyk et al. "Enzymatic Determination of Free Carnitine in Milk and Infant Formulas" Journal of AOAC International vol. 78, No. 1 (1995) p. 69–74.*
Marquis et al, "Enzymological determination of free carnitine concentrations in rat tissues", Journal of Lipid Research, vol. 41, 1964, pp. 184–187.
Cedarblad et al, "Excretion of L Carnitine in Man", Clinica Chimica ACTA., vol. 33, no. 1, 1971, pp. 117–123.
Seccombe et al, "Automated Method for L Carnitine Determination", Clinical Chemistry, vol. 22, no. 10, 1976, pp. 1589, 1592.

* cited by examiner

Primary Examiner—Jean C. Witz
Assistant Examiner—Susan Hanley
(74) Attorney, Agent, or Firm—Nixon & Vanderhye P.C.

(57) ABSTRACT

A kit for the determination of L-carnitine or short-chain acyl L-carnitines consisting of only two vials complete with all the necessary reactants, with the exception of standards, preferably the kit contains the reactants in lyophilized form.

10 Claims, No Drawings

KIT FOR THE DETERMINATION OF L-CARNITINE IN BIOLOGICAL FLUIDS AND TISSUES

This application is the US national phase of international application PCT/IT01/00166 filed 30 Mar. 2001 which designated the U.S.

The invention described herein relates to a kit for the determination of L-carnitine in biological fluids.

BACKGROUND TO THE INVENTION

L-carnitine plays a fundamental role in metabolism, being a key element in the oxidation of long-chain fatty acids and thus in the production of energy.

There are many pathological states the underlying cause of which is a deficiency of L-carnitine, and L-carnitine determination is necessary in order to establish the precise a etiology of the related disease processes.

There has been a growing awareness among clinicians over recent years of the importance of L-carnitine deficiencies (Bieber et is al. Fed. Proc. 41, 2858 (1982); Stanley, Adv. Pediatr. 34, 59 (1987).

One of the first methods used for determining L-carnitine (hereinafter called carnitine for short) was described by Marquis and Fritz in 1964 (Journal of Lipid Research 5, 184–187). Various other methods have been described, such as, for example, those by Marzo et al., J. Chromatogr. 527, 247 (1990); and Hoppel, in: Hommes (ed.), Techniques in Diagnostic Human Biochemical Genetics, New York, Wiley-Liss, 309–326 (1991).

The most widespread methods are based on the reaction of the enzyme carnitine acetyl transferase (CAT; EC 2.3.1.7):

One very widespread method for the indirect determination of carnitine is based on the reaction of acetyl-Coenzyme A, released by the preceding reaction with 5,5'-dithiobis-2-nitrobenzoate (DTNB), which in turn releases the thiophenylate ion, which is determined spectrophotometrically at 412 nm (see, in addition to the above-mentioned Marquis, Seccombe D. W., Clinical Chemistry, 22, No. 10, 1589–1592, 1976; Pearson, Methods of Enzymatic Analysis, 4, 1758–1771, 2nd edition—Bergmeyer; Casillas E. R. Biochimica et Biophysica Acta, 184, 566–577, 1969; Cederblad G. Clinica Chimica Acta, 33, 117.123, 1971; Carrier H. N., Muscle & Nerve July/August 326–328, 1980). This method determines free carnitine. For the determination of the short-chain acyl carnitines, and thus of total carnitines, the sample is subjected to alkaline hydrolysis, converting the acyl carnitines to free carnitine.

The known methods entail elaborate preparation phases, or use techniques which are only poorly conducive to automation of the analyses. For a discussion of the subject, see U.S. Pat. No. 5,316,917, filed in the name of Duke University, and incorporated herein for reference purposes. This patent aims to solve the problem of the automation of the analyses. This need is strongly felt in clinical laboratories that have to carry out large numbers of determinations. The Duke University patent offers the solution of an automated spectrophotometric method, consisting in the following steps:

1) addition of a plurality of samples of deproteinized biological fluids to a set of wells of a centrifugal spectrophotometric analyzer;

2) addition to each sample of:
   a) acetyl-Coenzyme A in an amount sufficient to react essentially with all the free carnitine in the sample to produce acetyl-carnitine and free Coenzyme A;
   b) DTNB in an amount sufficient to convert essentially all the Coenzyme A produced in the previous reaction to thiophenylate, and then
   c) simultaneously combine CAT, in each sample, in an amount sufficient to set off the reaction between acetyl-Coenzyme A and free carnitine and bring it to completion, and then
   d) determine the amount of thiophenylate present in the sample simultaneously by spectrophotometry.

The kit used to implement the method described in the patent cited includes:
   a) a first container containing a solution of DTNB at a concentration ranging from 0.27 to 27 mmol/L, at a pH ranging from 6.5 to 8.5, and
   b) a second container containing a solution consisting of acetyl-Coenzyme A at a concentration ranging from 1.2 to 120 mmol/L, where the two solutions can be mixed together prior to use to form a solution containing DTNB at a concentration ranging from 0.23 to 23 mmol/L and acetyl-Coenzyme A at a concentration ranging from 0.17 to 17 mmol/l.

In actual fact, the kit must also include a third container containing from 4 to 40 kU/L of CAT, for example in the form of a solution at a concentration ranging from 1.72 to 172 kU/L. It is envisaged that the third container should contain CAT in lyophilized form. Also envisaged in the kit are containers with carnitine standards in aqueous solution from 0.1 to 10 mmol/L and of octanoyl L-carnitine from 0.1 to 10 mmol/L. Also provided in the kit is a fourth container containing a 3-[N-morpholine]propanesulphonic acid hydrochloric solution, from 0.1 to 10 mmol/L.

The execution of the procedure entails the preparation of 4 solutions:
1. DTNB; HEPES; EDTA at pH 7.5
2. MOPS-HCl
3. KOH In fact, the procedure described in the patent is called "three reagent chemistry".

It is known that the solutions envisaged in the kit described above must be stored at low temperature, from 0 to 4° C., as prescribed in the patent cited.

U.S. Pat. No. 6,027,690, a divisional patent of U.S. Pat. No. 5,872,008, filed in the name of Bair and Shug, provides a kit for the diagnosis of premenstrual syndrome, based on the determination of free and total carnitine in the blood. Apart from the specific indication of the method, to implement the method the kit consists of:
   a) a first container containing a solution of acetyl-Coenzyme A at a concentration ranging from 1.2 to 120 mmol/L, and
   b) a second container containing a solution consisting of DTNB or N-(p-2(benzimidazolyl)phenyl)maleimide at a concentration ranging from 0.27 to 27 mmol/L at a pH ranging from 6.5 to 8.5, where the two solutions can be mixed together prior to use to form a solution consisting of DTNB or N-(p-2(benzimidazolyl)phenyl) maleimide at a concentration ranging from 0.23 to 23 mmol/L and acetyl-Coenzyme A at a concentration ranging from 0.17 to 17 mmol/l.

In the execution of the procedure according to U.S. Pat. No. 6,072,690, the method described in U.S. Pat. No. 5,316,917 can be adopted amongst others.

A Boehringer Mannheim kit is commercially available for the determination of L-carnitine in plasma, seminal fluid, and urine. The determination is based on the following reactions:

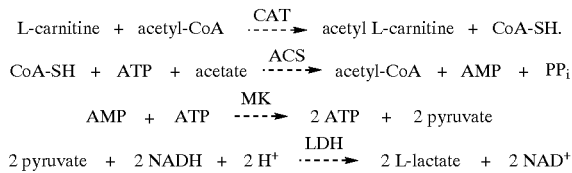

The amount of NADH consumed during the reaction is equivalent to half the amount of L-carnitine. NADH is determined by absorbance at 334 (Hg), 340 or 365 (Hg) nm.

The kit comprises:
1) 3 vials (1) each containing 0.7 g of a Coenzyme/buffer mixture consisting of Tris buffer pH 7.0, NADH 5 mg, ATP 6 mg, acetyl-Coenzyme A 4 mg, PEP 3 mg, magnesium acetate, and stabilizing agents.
2) Vial (2) containing approximately 3 ml of enzyme suspension consisting of acetyl-CoA synthetase (ACS), 2U approx., myokinase (MK), 160 U approx., lactate dehydrogenase (LDH), 240 U approx., and pyruvate kinase (PK), 240 U approx.
3) Vial (3) containing 0.2 ml of carnitine acetyl transferase (CAT) enzyme suspension, 60 U approx.
4) Vial (4) containing L-carnitine standard.
5) Vial (5) containing detergent solution.

Prior to use, the contents of one vial (1) are diluted with 10 ml of distilled water and 1 ml is added from vial (5). The other vials are used as such. The procedure consists in the addition of the sample (or standard) to solution (1), then addition of suspension (2), measurement of absorbance, then addition of suspension (3) and subsequent measurement of absorbance.

BRIEF SUMMARY OF THE INVENTION

It has now been found that it is possible to provide a kit for the determination of L-carnitine or short-chain acyl L-carnitines consisting of only two vials complete with all the necessary reactants, with the exception of the standards. Conveniently, the kits contain the reactants in lyophilized form.

One of the advantages afforded by the realization of the invention described herein consists in the possibility of determining carnitine over a broad range of concentrations.

The kit according to the invention comprises:
a) a first container containing Reagent 1, said Reagent 1 consisting of HEPES, EDTA, acetyl-Coenzyme A and DTNB;
b) a second container containing Reagent 2, said Reagent 2 consisting of carnitine acetyl transferase.

Therefore, one subject of the invention described herein is a kit for the determination of L-carnitine in biological tissues and fluids, its use for the determination of L-carnitine in biological tissues and fluids and methods for the determination of L-carnitine in biological tissues and fluids using the kit.

According to the invention described herein, the kit permits the determination of L-carnitine in biological fluids and tissues. Examples of biological fluids and tissues are blood, plasma and seminal fluid. When suitably treated according to conventional techniques, other tissues can be analyzed with the kit according to the invention.

DETAILED DESCRIPTION OF THE INVENTION

In a first preferred form, Reagent 1 consists of:

| HEPES | 0.1 M, pH 7.5 |
| EDTA | 50 mM, pH 7 |
| acetyl-Coenzyme A | |
| DTNB | 10, 1 mM |

Preferably, Reagent 1 has the following composition per ml:

| HEPES | 0.1 M, pH 75 | 0.652 mL |
| EDTA | 50 mM, pH 7 | 0.174 mL |
| acetyl-Coenzyme A | | 0.087 mL |
| DTNB | 10.1 mM | 0.087 mL |

The Reagent 1 container preferably contains 3 mL of Reagent 1.

In a first preferred form, Reagent 2 consists of:
carnitine acetyl transferase 0.500 mL If deemed appropriate, the kit may also contain other elements such as L-carnitine standards, other reactants for the preparation of samples, e.g. plasma or seminal fluid. Reagents 1 and 2 may also essentially contain, in addition to the basic reactants necessary for the reactions, i.e. acetyl-Coenzyme A, DTNB and carnitine acetyl transferase, additional substances useful for the analysis, or alternative substances to those contained in the kit capable of producing the same effect, e.g. buffers, chelating agents, complexing agents, pH correctors, preservatives, and stabilizing agents. Any changes or improvements to the kit supplied on the basis of the invention described herein, which substantially lead to the same result and afford the same advantages fall within the compass of the invention described herein.

The preferred form of the kit is that in which the reagents are in lyophilized form. This form permits prolonged storage of the reagents in normal ambient conditions, without particular precautions, with obvious advantages from the point of view of the marketing of the kit. The lyophilization is done according to the conventional techniques used in the field and requires no further description.

The kit according to a first embodiment of the invention described herein (3 mL of Reagent 1 and 0.500 mL of Reagent 2) is sufficient for approximately 13 determinations, if the manual method is used, or for approximately 60 determinations, if the automatic method is used. Both methods are described in detail here below.

A first preferred embodiment of the invention described herein relates to the determination of carnitine in plasma.

The invention described herein is based on the reaction that takes place between L-carnitine and acetyl-CoA in the presence of the enzyme carnitine acetyl transferase (CAT). The Coenzyme A (CoA) produced by this reaction reacts in turn with 5.5°-dithiobis-2-nitrobenzoate (DTNB), releasing thiophenylate ions (TNB−) which absorb at a wavelength of 412 nm, in the case of the use of a manual spectrophotometer, or at a wavelength of 405 nm, in the case of the use of an automatic-type spectrophotometer. The reactions involved are all quantitative, and therefore the TNB− absorbance value can be used to determine the carnitine concentration in the sample.

The invention is illustrated with reference to a preferred form of its embodiment, namely for the determination of carnitine in plasma. It is understood that the principles involved in the invention described herein are equally applicable to other tissues, which are treated according to their nature, using conventional procedures which are a matter of general knowledge to people with average experience in the field. The determination method comprises the following steps:

a) deproteinizing of the plasma sample in an acid milieu;
b) neutralization of the sample;
c) incubation.

It is in step c) that the enzymatic reactions occur using the kit according to the invention described herein:

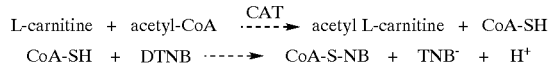

The amount of TNB− ions forming in the latter reaction is equivalent to that of the L-carnitine initially present in the sample.

Ambient pH weakly influences the reactions and therefore the result of the analysis; in fact, at pH above 8.5 CAT is inactivated, whereas at pH values below 7 the dissociation of DTNB is incomplete, and therefore the L-carnitine values will be underestimated.

As an alternative to steps a) and b) described above, the sample can be deproteinized by simple filtration.

EXAMPLE 1

Preparation of Solutions

Acetyl-CoA 12.35 mM: solubilize 86 mg of acetyl-CoA in 8.6 mL of bidistilled water. This solution will be used to prepare Reagent 1.

Carnitine acetyl-transferase (CAT): dilute the CAT with bidistilled water (1 volume of CAT+11 volumes of bidistilled water). This solution will be used to prepare Reagent 2. If not used immediately, the reagent can be stored at −20° C. and defrosted at the time of use.

EDTA 50 mM pH 7.0: solubilize 2.2 g of EDTA in 50 mL of bidistilled water in a 100 mL calibrated flask. Bring the pH to 7.0 with glacial acetic acid and top up to volume with bidistilled water. The solution is stable for 6 months at 4° C.

DTNB 10 mM: solubilize 34.4 mg of DTNB with 8.6 ml of Hepes 0.1 M at pH 7.5.

Hepes 0.1 M at pH 7.5: solubilize 2.38 g of Hepes in 50 mL of bidistilled water in a 100 mL calibrated flask. Bring the pH to 7.5 with potash 1.25 M, and top up to volume with bidistilled water. The solution is stable for 6 months at 4° C.

Perchloric acid 2.75 M: dilute 23.2 mL of 70% perchloric acid in bidistilled water in a 100 mL calibrated flask. The solution is stable for 6 months at ambient temperature.

Potassium carbonate 1.2 M: solubilize 16.6 g of potassium carbonate with 80 mL of bidistilled water. Mix and top up to volume with bidistilled water. The solution is stable for 6 months at ambient temperature.

Potassium hydroxide 1.25 M: solubilize 8.25 g of potassium hydroxide with 80 mL of bidistilled water a 100 mL calibrated flask. Mix and top up to volume with bidistilled water. The solution is stable for 6 months at ambient temperature.

Reagent 1: prepare 100 mL of reagent: to 65.5 mL of Hepes 0.1 M at pH 7.5 add 17.3 mL of EDTA 50 mM, pH 7.0, 8.6 mL of DTNB 10 mM and 8.6 mL of acetyl-CoA 12.35 mM. The solution is stable for 6 months at −20° C.

Deproteinizing of Plasma/Serum and Neutralization of Sample

Transfer 300 μL of plasma/serum and 40 μL of perchloric acid 2.75 M into a 1.5 ml Eppendorf tube. Mix well and then centrifuge at 10,000×g for 5 min at 4° C. Transfer 250 μL of the supernatant and add 40 μL of potassium carbonate 1.2 M in a 1.5 ml Eppendorf tube. Mix and then leave the samples to digest in ice for 10 min. Centrifuge again at 10,000×g for 5 min at 4° C. Remove the supernatant for analysis.

Deproteinizing of Plasma/Serum by Filtration

Load the sample of plasma/serum on AMICON type filters with cut-off ranging from 5000 to 20000 NMW. Load the sample (400 μL approx.) in an Eppendorf tube containing the filter, to be centrifuged at 15000×g for 30–40 minutes at 4° C. Remove the filtrate for analysis.

Enzymatic Analysis

A) Manual type spectrophotometry.
Varian DMS-80 UV/VIS spectrophotometer
Wavelength: 412 nm
Cuvette: single-use, disposable, 1 cm optical path
Temperature: 20–25° C.
Measurement: against air.
Incubation:
transfer to cuvette

|  | Blank (μL) | Sample (μL) |
|---|---|---|
| Bidistilled water | 1000 | 750 |
| Sample | — | 250 |
| Reagent 1 | 230 | 230 |

Stir. After 5 minutes measure the absorbance of the blank and the sample ($A_1$). On completion of reading, add 20 μL of CAT (Reagent 2) to each test tube and mix. After another 10 minutes repeat the measurement of the blank and the sample ($A_2$).

The concentration is calculated as follows:

$$C = \frac{\Delta A}{\varepsilon \times d} \times F \times 1000$$

where:

C=concentration of sample (nmol/mL)
$\Delta A = (A_2-A_1)_{sample} - (A_2-A_1)_{blank}$
$\varepsilon$=coefficient of molar extinction of TNB−

(412 nm=13.6 L×μmol$^{-1}$×cm)

d=optical path length (cm)
F=dilution factor (6.55)
1000=conversion factor to obtain the result in nmol/mL.
Example of calculation:

|  | $A_1$ | $A_2$ | $A_2-A_1$ |
|---|---|---|---|
| Blank | 0.169 | 0.172 | 0.003 |
| Sample | 0.170 | 0.242 | 0.072 |

Applying the formula indicated above: C=33.2 nmol/mL.

B) Automatic Type Spectrophotometer

Before starting the analysis, dilute Reagent 1 and Reagent 2 5 times with bidistilled water (e.g., to 1 mL of Reagent 1 add 4 mL of bidistilled water; to 1 mL of Reagent 2 add 4 mL of bidistilled water).

Experimental Conditions

Procedure for programming the Roche mod. Cobas-Mira S automatic analyzer (software used N* 8347)

| FREE CARNITINE | |
|---|---|
| SW 884*7 | COBAS MIRA S |
| GENERAL | |
| MEASUREMENT MODE | ABSORB |
| REACTION MODE | D-R-S-SRI |
| CALIBRATION MODE | LIN REGR |
| REAGENT BLANK | REAG/SOL |
| CLEANER | NO |
| WAVELENGTH | 405 nm |
| DECIMAL POSITION | 2 |
| UNIT | µmol/L |
| ANALYSIS | |
| DILUTION NAME | H₂O |
| FACTOR | NO |
| TIME | NO |
| STD: | MAIN DIRECT |
| MAIN STD | 200 µmol/L |
| POST DIL FACTOR | 3 |
| CONC. FACTOR | NO |
| SAMPLE CYCLE | 1 |
| VOLUME | 50 µL |
| DILUTION NAME | H₂O |
| VOLUME | 10 µL |
| REAGENT CYCLE | 1 |
| VOLUME | 250 µL |
| START R1 CYCLE | 7 |
| VOLUME | 40 µL |
| DILUTION NAME | H₂O |
| VOLUME | 10 µL |
| CALCULATION | |
| SAMPLE LIMIT | 0.1 |
| POINT | T1 |
| REAC. DIRECTION | INCREASE |
| CHECK | ON |
| CONVERS. FACTOR | 1 |
| OFFSET | 0 |
| TEST RANGE LOW | ON |
| HIGH | ON |
| NORMAL RANGE LOW | YES |
| HIGH | NO |
| NUMBERS OF STEPS | 1 |
| CALC. STEP A | ENDPOINT |
| FIRST READING | 6 |
| LAST READING | 30 |

| FREE CARNITINE | |
|---|---|
| CALIBRATION | |
| CALIB. INTERVAL | ON REQUEST |
| BLANK | |
| REAGENT RANGE LOW | −0.0001 |
| HIGH | 0.1000 |
| BLANK RANGE LOW | −0.0050 |
| HIGH | 0.0050 |
| STANDARD POS: | 1 |
| 1: 200 µmol/L | 2: 100 µmol/L |
| 3: 75 µmol/L | 4: 50 µmol/L |
| 5: 30 µmol/L | 6: 20 µmol/L |
| 7: 10 µmol/L | 8: 0 µmol/L |
| REPLICATE | DUPLICATE |
| DEVIATION | 10% |
| CORRECTION STD | NO |
| CONTROL | |
| CS1* POS: 11 LOW | 90 mol/L |
| ASSIGN | 100 µmol/L |
| HIGH | 110 µmol/L |
| CS2* POS: 12 LOW | 40 µmol/L |
| ASSIGN | 50 µmol/L |
| HIGH | 60 µmol/L |
| CS3* POS: 13 LOW | 12 µmol/L |
| ASSIGN | 20 µmol/L |
| HIGH | 28 µmol/L |

Note: the samples called CS1, CS2 e CS3 refer to the reference standards and are prepared by scalar dilution of the mother solution of L-carnitine inner salt at a concentration of 200 µmol/L.

The calculation of the concentrations of the blanks is done automatically by the analyzer which extrapolates them from a straight calibration line to be prepared fresh for each analysis session (possibly in duplicate).

The above-described sample preparation and analysis conditions being equal, it is possible to calculate the carnitine concentration for an unknown sample immediately by multiplying its absorbance value by the factor 1028.382. In this case neither the calibration line nor the control samples will be used.

Whenever the unknown samples have been deproteinized by acidification and subsequent neutralization with the procedure described above, the value of the concentration obtained must be multiplied by the factor 1.3146.

Given here below, by way of an example, is a table directly correlating the L-carnitine concentrations with the absorbance readings.

| CALCULATION OF L-CARNITINE CONCENTRATIONS USING THE FACTOR 481.62 | | | | | | | | | | | |
|---|---|---|---|---|---|---|---|---|---|---|---|
| Abs | µmoli/L | Abs | µmoli/L | Abs | µmoli/L | Abs | µmoli/L | Abs | µmoli/L | Abs | µmoli/L |
| 0.001 | 0.482 | 0.051 | 24.563 | 0.101 | 48.644 | 0.151 | 72.725 | 0.201 | 96.806 | 0.251 | 120.89 |
| 0.002 | 0.963 | 0.052 | 25.044 | 0.102 | 49.125 | 0.152 | 73.206 | 0.202 | 97.287 | 0.252 | 121.37 |
| 0.003 | 1.445 | 0.053 | 25.526 | 0.103 | 49.607 | 0.153 | 73.688 | 0.203 | 97.769 | 0.253 | 121.85 |
| 0.004 | 1.926 | 0.054 | 26.007 | 0.104 | 50.088 | 0.154 | 74.169 | 0.204 | 98.250 | 0.254 | 122.33 |
| 0.005 | 2.408 | 0.055 | 26.489 | 0.105 | 50.570 | 0.155 | 74.651 | 0.205 | 98.732 | 0.255 | 122.81 |
| 0.006 | 2.890 | 0.056 | 26.971 | 0.106 | 51.052 | 0.156 | 75.133 | 0.206 | 99.214 | 0.256 | 123.29 |
| 0.007 | 3.371 | 0.057 | 27.452 | 0.107 | 51.533 | 0.157 | 75.614 | 0.207 | 99.695 | 0.257 | 123.78 |
| 0.008 | 3.853 | 0.058 | 27.934 | 0.108 | 52.015 | 0.158 | 76.096 | 0.208 | 100.18 | 0.258 | 124.26 |
| 0.009 | 4.335 | 0.059 | 28.416 | 0.109 | 52.497 | 0.159 | 76.578 | 0.209 | 100.66 | 0.259 | 124.74 |
| 0.010 | 4.816 | 0.060 | 28.897 | 0.110 | 52.978 | 0.160 | 77.059 | 0.210 | 101.14 | 0.260 | 125.22 |
| 0.011 | 5.298 | 0.061 | 29.379 | 0.111 | 53.460 | 0.161 | 77.541 | 0.211 | 101.62 | 0.261 | 125.70 |
| 0.012 | 5.779 | 0.062 | 29.860 | 0.112 | 53.941 | 0.162 | 78.022 | 0.212 | 102.10 | 0.262 | 126.18 |
| 0.013 | 6.261 | 0.063 | 30.342 | 0.113 | 54.423 | 0.163 | 78.504 | 0.213 | 102.59 | 0.263 | 126.67 |

-continued

CALCULATION OF L-CARNITINE CONCENTRATIONS USING THE FACTOR 481.62

| Abs | μmoli/L | Abs | μmoli/L | Abs | μmoli/L | Abs | μmoli/L | Abs | μmoli/L | Abs | μmoli/L |
|---|---|---|---|---|---|---|---|---|---|---|---|
| 0.014 | 6.743 | 0.064 | 30.824 | 0.114 | 54.905 | 0.164 | 78.986 | 0.214 | 103.07 | 0.264 | 127.15 |
| 0.015 | 7.224 | 0.065 | 31.305 | 0.115 | 55.386 | 0.165 | 79.467 | 0.215 | 103.55 | 0.265 | 127.63 |
| 0.016 | 7.706 | 0.066 | 31.787 | 0.116 | 55.868 | 0.166 | 79.949 | 0.216 | 104.03 | 0.266 | 128.11 |
| 0.017 | 8.188 | 0.067 | 32.269 | 0.117 | 56.350 | 0.167 | 80.431 | 0.217 | 104.51 | 0.267 | 128.59 |
| 0.018 | 8.669 | 0.068 | 32.750 | 0.118 | 56.831 | 0.168 | 80.912 | 0.218 | 104.99 | 0.268 | 129.07 |
| 0.019 | 9.151 | 0.069 | 33.232 | 0.119 | 57.313 | 0.169 | 81.394 | 0.219 | 105.47 | 0.269 | 129.56 |
| 0.020 | 9.632 | 0.070 | 33.713 | 0.120 | 57.794 | 0.170 | 81.875 | 0.220 | 105.96 | 0.270 | 130.04 |
| 0.021 | 10.114 | 0.071 | 34.195 | 0.121 | 58.276 | 0.171 | 82.357 | 0.221 | 106.44 | 0.271 | 130.52 |
| 0.022 | 10.596 | 0.072 | 34.677 | 0.122 | 58.758 | 0.172 | 82.839 | 0.222 | 106.92 | 0.272 | 131.00 |
| 0.023 | 11.077 | 0.073 | 35.158 | 0.123 | 59.239 | 0.173 | 83.320 | 0.223 | 107.40 | 0.273 | 131.48 |
| 0.024 | 11.559 | 0.074 | 35.640 | 0.124 | 59.721 | 0.174 | 83.802 | 0.224 | 107.88 | 0.274 | 131.96 |
| 0.025 | 12.041 | 0.075 | 36.122 | 0.125 | 60.203 | 0.175 | 84.254 | 0.225 | 108.36 | 0.275 | 132.45 |
| 0.026 | 12.522 | 0.076 | 36.603 | 0.126 | 60.684 | 0.176 | 84.765 | 0.226 | 108.85 | 0.276 | 132.93 |
| 0.027 | 13.004 | 0.077 | 37.085 | 0.127 | 61.166 | 0.177 | 85.247 | 0.227 | 109.33 | 0.277 | 133.41 |
| 0.028 | 13.485 | 0.078 | 37.566 | 0.128 | 61.647 | 0.178 | 85.728 | 0.228 | 109.81 | 0.278 | 133.89 |
| 0.029 | 13.967 | 0.079 | 38.048 | 0.129 | 62.129 | 0.179 | 86.210 | 0.229 | 110.29 | 0.279 | 134.37 |
| 0.030 | 14.449 | 0.080 | 38.530 | 0.130 | 62.611 | 0.180 | 86.692 | 0.230 | 110.77 | 0.280 | 134.85 |
| 0.031 | 14.930 | 0.081 | 39.011 | 0.131 | 63.092 | 0.181 | 87.173 | 0.231 | 111.25 | 0.281 | 135.34 |
| 0.032 | 15.412 | 0.082 | 39.493 | 0.132 | 63.574 | 0.182 | 87.655 | 0.232 | 111.74 | 0.282 | 135.82 |
| 0.033 | 15.893 | 0.083 | 39.974 | 0.133 | 64.055 | 0.183 | 88.136 | 0.233 | 112.22 | 0.283 | 136.30 |
| 0.034 | 16.375 | 0.084 | 40.456 | 0.134 | 64.537 | 0.184 | 88.618 | 0.234 | 112.70 | 0.284 | 136.78 |
| 0.035 | 16.857 | 0.085 | 40.938 | 0.135 | 65.019 | 0.185 | 89.100 | 0.235 | 113.18 | 0.285 | 137.26 |
| 0.036 | 17.338 | 0.086 | 41.419 | 0.136 | 65.500 | 0.186 | 89.581 | 0.236 | 113.66 | 0.286 | 137.74 |
| 0.037 | 17.820 | 0.087 | 41.901 | 0.137 | 65.982 | 0.187 | 90.063 | 0.237 | 114.14 | 0.287 | 138.22 |
| 0.038 | 18.302 | 0.088 | 42.383 | 0.138 | 66.464 | 0.188 | 90.545 | 0.238 | 114.63 | 0.288 | 138.71 |
| 0.039 | 18.783 | 0.089 | 42.864 | 0.139 | 66.945 | 0.189 | 91.026 | 0.239 | 115.11 | 0.289 | 139.19 |
| 0.040 | 19.265 | 0.090 | 43.346 | 0.140 | 67.427 | 0.190 | 91.508 | 0.240 | 115.59 | 0.290 | 139.67 |
| 0.041 | 19.746 | 0.091 | 43.827 | 0.141 | 67.908 | 0.191 | 91.989 | 0.241 | 116.07 | 0.291 | 140.15 |
| 0.042 | 20.228 | 0.092 | 44.309 | 0.142 | 68.390 | 0.192 | 92.471 | 0.242 | 116.55 | 0.292 | 140.63 |
| 0.043 | 20.710 | 0.093 | 44.791 | 0.143 | 68.872 | 0.193 | 92.953 | 0.243 | 117.03 | 0.293 | 141.11 |
| 0.044 | 21.191 | 0.094 | 45.272 | 0.144 | 69.353 | 0.194 | 93.434 | 0.244 | 117.52 | 0.294 | 141.60 |
| 0.045 | 21.673 | 0.095 | 45.754 | 0.145 | 69.835 | 0.195 | 93.916 | 0.245 | 118.00 | 0.295 | 142.08 |
| 0.046 | 22.155 | 0.096 | 46.236 | 0.146 | 70.317 | 0.196 | 94.398 | 0.246 | 118.48 | 0.296 | 142.56 |
| 0.047 | 22.636 | 0.097 | 46.717 | 0.147 | 70.798 | 0.197 | 94.879 | 0.247 | 118.96 | 13.297 | 143.04 |
| 0.048 | 23.118 | 0.098 | 47.199 | 0.148 | 71.280 | 0.198 | 95.361 | 0.248 | 119.44 | 0.298 | 143.52 |
| 0.049 | 23.599 | 0.099 | 47.680 | 0.149 | 71.761 | 0.199 | 95.842 | 0.249 | 119.92 | 0.299 | 144.00 |
| 0.050 | 24.081 | 0.100 | 48.162 | 0.150 | 72.243 | 0.200 | 96.324 | 0.250 | 120.41 | 0.300 | 144.49 |

What is claimed is:

1. Kit for the determination of L-carnitine in biological fluids and tissues, consisting essentially of:
   a) a first container containing Reagent 1, said Reagent 1 being in lyophilized form or in a solution kept at −20° C. and consisting essentially of:

| HEPES | 0.1 M, pH 7.5 |
|---|---|
| EDTA | 50 mM, pH 7 |
| acetyl-Coenzyme A | |
| DTNB | 10.1 mM | b) a second container containing Reagent 2, said Reagent 2 comprising carnitine acetyl transferase.

2. Kit for the determination of L-carnitine in biological fluids and tissues, consisting essentially of:
   a) a first container containing Reagent 1, said Reagent 1 being in lyophilized form or in a solution kept at −20° C. and consisting of:

| HEPES | 0.1 M, pH 75 | 0.652 mL |
|---|---|---|
| EDTA | 50 mM, pH 7 | 0.174 mL |
| acetyl-Coenzyme A | | 0.087 mL |
| DTNB | 10.1 mM | 0.087 mL | b) a second container containing Reagent 2, said Reagent 2 comprising carnitine acetyl transferase.

3. Kit according to claim 2, in which said first container contains 3 ml of said Reagent 1.

4. Kit according to claim 1 or 2, in which said container contains 0.500 ml of said Reagent 2.

5. Kit according to claim 1 or 2, which additionally comprise containers containing L-carnitine standards.

6. Kit according to claim 1 or 2, in which the reagents of the second container are in lyophilized form.

7. Method for the determination of total carnitines in a biological tissue or fluid, comprising the steps of:
   a) subjecting a sample of said biological tissues or fluids to alkaline hydrolysis; and
   b) determining L-carnitine in said biological tissue or fluid using the kit according to claim 1.

8. Method according to claim 7, wherein said fluid is selected from the group consisting of plasma, seminal fluid and urine.

9. Method for the determination of total carnitines in a biological tissue or fluid, comprising the steps of:
   a) subjecting a sample of said biological tissues or fluids to alkaline hydrolysis; and
   b) determining L-carnitine in said biological tissue or fluid using the kit according to claim 2.

10. Method according to claim 9, wherein said fluid is selected from the group consisting of plasma, seminal fluid and urine.

* * * * *